(12) United States Patent
East et al.

(10) Patent No.: US 6,235,037 B1
(45) Date of Patent: May 22, 2001

(54) SURGICAL APPARATUS

(75) Inventors: Michael C. East; Suzanne H. Suckling, both of Christchurch (NZ)

(73) Assignee: West-Walker Bennett, Wellington (NZ)

( * ) Notice: Subject to any disclaimer, the term of this patent is extended or adjusted under 35 U.S.C. 154(b) by 0 days.

(21) Appl. No.: 09/194,519

(22) PCT Filed: May 23, 1997

(86) PCT No.: PCT/NZ97/00066

§ 371 Date: Sep. 13, 1999

§ 102(e) Date: Sep. 13, 1999

(87) PCT Pub. No.: WO97/45053

PCT Pub. Date: Dec. 4, 1997

(30) Foreign Application Priority Data

| May 24, 1996 | (NZ) | 286667 |
| May 27, 1996 | (NZ) | 286672 |
| Feb. 13, 1997 | (NZ) | 314233 |
| May 13, 1997 | (NZ) | 314807 |

(51) Int. Cl.$^7$ ................................. A61B 17/42
(52) U.S. Cl. ........................................... 606/119
(58) Field of Search ............... 604/23, 26, 96.01; 606/108, 119, 192, 193; 600/207

(56) References Cited

U.S. PATENT DOCUMENTS

| 3,882,852 | * | 5/1975 | Sinnreich | 128/4 |
| 5,002,557 | * | 3/1991 | Hasson | 604/26 |
| 5,188,630 | * | 2/1993 | Christoudias | 604/96.01 |
| 5,338,297 | * | 8/1994 | Kocur et al. | 604/193 |
| 5,445,645 | * | 8/1995 | Debbas | 606/192 |
| 5,458,612 | * | 10/1995 | Chin | 606/192 |
| 5,643,285 | * | 7/1997 | Rowden et al. | 606/119 |
| 5,704,372 | * | 1/1998 | Moll et al. | 606/192 |

* cited by examiner

Primary Examiner—Gene Mancene
Assistant Examiner—Eduardo C. Robert
(74) Attorney, Agent, or Firm—Wilson Sonsini Goodrich & Rosati; David J. Abraham

(57) ABSTRACT

A surgical apparatus including a housing with a handle end and a manipulation end, a rotatable manipulation mechanism guided within the housing and extendible beyond the end of the housing, an inflatable diaphragm situated on the housing and a channel for passing a gas through or along the manipulation mechanism from the handle end of the housing to the manipulation end. The invention is also directed to a method of performing laparoscopically-assisted vaginal hysterectomies using the apparatus.

8 Claims, 5 Drawing Sheets

SURGICAL APPARATUS

TECHNICAL FIELD

The invention relates to a surgical apparatus for use in laparoscopy assisted vaginal hysterectomies.

BACKGROUND ART

Hysterectomies have traditionally been performed by making a cut through the abdomen wall, freeing up the uterus and removing the uterus through the cut in the wall. In more recent times some hysterectomies have been able to be performed through the vaginal opening which consists in freeing up the uterus by using laparoscopic instruments and then removing the uterus through an opening made at the top of the vagina.

Laparoscopic procedures require the abdomen to be inflated with gas, to form a pneumoperitoneum, which enables the surgeon to see what needs to be done and easily move the instruments around and position them to make the necessary cuts, sutures etc. Thus laparoscopically assisted vaginal hysterectomy (LAVH) is considered an advanced laparoscopic operative procedure.

One difficulty with LAVH procedures is that once the cut is made at the top of the vagina in order to allow the uterus to be removed, the gas in the abdomen escapes, making it difficult and time consuming to finally release the uterus from the abdomen (cut ligaments etc) and remove it through the vaginal opening. Therefore, although LAVH allows patients to avoid undergoing abdomen hysterectomy procedures, thus affording them a more rapid recovery, the vaginal portion of the operation can still be extremely difficult if there is little descent of the cervix, especially when the uterus is very large. In such instances the vaginal portion of the surgery can take almost as long as the laparoscopic portion and can cause great stress to the surgeon and lead to significant blood loss. The more dissection performed laparoscopically, the easier the vaginal component of the surgery. Therefore, the longer the pneumoperitoneum can be maintained the more efficient the procedure becomes. Bleeding and/or damage to the ureter is also a significant problem. Formation of the "bladder flap" can be difficult and hazardous with perforation of the bladder on occasions occurring. However, the bladder has to be disected off the lower segment of the uterus before the uterine arteries can be approached. In an attempt to make the "bladder flap" dissection easier, the initial dissection has been performed vaginally without opening the peritoneal fold of the utero-vesical space. However, if the fold of the peritoneum is breached, then gas can escape from the abdomen into the vagina thus deflating the abdomen and making it impossible to continue the surgery. In order to minimise this problem saline packs have been placed into the vagina in an attempt to slow down gas leak, but rarely does this prove to be satisfactory.

In addition to this, in order for the hysterectomy procedure to be completed efficiently via the laparoscope, it is necessary to manipulate certain organs in order to obtain access to make the necessary cuts, sutures etc. For example, it may be necessary to push the uterus high up into the abdomen to free the ligaments for access by the surgeon.

A further difficulty occurs in forming the pneumoperitoneum as standard techniques usually involve the blind insertion of the gas used via a Verres needle. As this is a blind insertion of the gas, the operator cannot have complete confidence in where the gas is being inserted.

Sabella et al in Obstet. Gynecol. 1996:87:465 entitled "A Technique for Laparoscopic Completion of Vaginal Hysterectomy" disclosed a uterine manipulator including an inflatable cuff that seals the vaginal orifice thus maintaining the pneumoperitoneum.

The technique described by Sabella et al involves proceeding with a vaginal hysterectomy until the opening of the peritoneal reflections and ligature of uterine vessels and uterosacral ligaments. It is at this point, if laparoscopic assistance becomes necessary, that the uterine manipulator with inflatable cuff is inserted vaginally, allowing completion of the operation laparoscopically.

The uterine manipulator described in the Sabella article suffers from a number of deficiencies. Once the cuff is inflated the uterine manipulator is fixed in position. The manipulator can only be restrictively manoevered about that point and cannot readily extend the uterus further into the pelvis. There is no disclosure of any uterine manipulation means able to move independently in relation to the apparatus once the cuff is inflated. The Sabella device therefore, does not make it easy to stretch out the tissue between the cervix and the vagina that it is to be transected with, via stapling device or diathermy for example, while maintaining the pneumoperitoneum. In addition, the surgeon will be operating in close proximity to the inflated cuff increasing the inherent risk of puncture and losing the pneumoperitoneum.

European Patent Application 0642766 to the United States Surgical Corporation discloses a manipulator apparatus for use in hysterectomy procedures that also includes an inflatable member. This apparatus utilises the inflatable member to engage the uterine wall in order to position the uterus for examination purposes. The inflatable member is not used to seal the vaginal orifice and there is no disclosure of any uterine manipulation means able to move independently of the inflatable member.

There is therefore a need for a device capable of maintaining a pneumoperitoneum throughout LAVH procedures. There is also a need for a device which will maintain a pneumoperitoneum together with providing means to manipulate the uterus as may be necessary during the LAVH procedure. There is also a need for a device which can improve the creation of a pneumoperitoneum during LAVH procedures.

The field of surgery is also beginning to utilise mechanical means, such as robotic manipulation, for assisting surgeons in performing surgical procedures. This technology involves the surgeon directing the robotic mechanical manipulation means during the performance of a surgical procedure. In order for hysterectomies and other uterine procedures to be able to utilise this technology, it will be advantageous if not essential to provide a fixed fulcrum point about which and from which the manipulation device can be moved.

It is an object of the invention to go some way to meeting the identified needs or to provide the public with a useful choice.

SUMMARY OF THE INVENTION

In one aspect, the invention relates to a surgical apparatus comprising an elongated housing, having a handle end and a manipulation end; a bore extending through the housing; a manipulation means comprising a rod which extends through the bore in the housing with an end portion which extends from a manipulation end of the housing, which rod is reciprocally movable and rotatable within the bore of the housing to enable an end portion of the rod to be further extended from or retracted towards and rotated about the manipulation end of the housing, the end portion of the rod portion having a tip; a diaphragm situated distal to a handle end of the housing and adapted to be inflated and deflated substantially circumferentially from the housing; and a channel for passing a gas from the end portion of the rod past the diaphragm, extending along or through the rod and having an exit in or adjacent to the end portion of the rod between the manipulation end of the housing and the tip of the rod.

In another aspect, the invention relates to a surgical apparatus comprising an elongated housing having a handle end and a manipulation end; a bore extending through the housing; manipulation means comprising a rod adapted to reciprocate and rotate within the bore and having a handle on one end of the housing and a portion which extends from and retracts towards a manipulation end of the housing at another end of the housing, the portion having a tip; a diaphragm situated distal to a handle end of the housing and adapted to be inflated and deflated substantially circumferentially from the housing via a passage associated with the bore; and a gas channel passing through the rod and having an exit from a portion of the rod between the manipulation end of the housing and the tip of the rod.

In still another aspect, the invention relates to a method of laparoscopically assisted vaginal hysterectomy, the method utilizing a surgical apparatus which includes a diaphragm adapted to be inflated and deflated substantially circumferentially from a housing; a rod which extends through the housing and from a manipulation end of the housing and which can rotate and reciprocate in relation to the housing, and a gas channel which extends through the rod, the method comprising the steps of inserting the apparatus with a diaphragm in a deflated condition into a vagina; inflating the diaphragm to fix the apparatus in position and to seal the vagina; passing a gas through the gas channel and into a peritoneal and abdominal cavity to create a pneumoperitoneum; utilizing the rod to manipulate the uterus from within a uterus prior to the vaginal cut; and utilizing the rod to manipulate the uterus from outside the uterus after the vaginal cut.

The invention comprises a surgical apparatus including:
a housing,
a diaphragm adapted to be inflated substantially circumferentially around the housing, and
manipulation means guided within the housing and adapted to extend substantially longitudinally from the housing and to rotate and reciprocate in relation to the housing.

Preferably means associated with the housing will communicate the diaphragm with a fluid source by which the diaphragm can be inflated.

Preferably the invention comprises a surgical apparatus comprising:
an elongated housing having a handle end and a manipulation end,
a bore extending through the housing,
manipulation means comprising a rod adapted to reciprocate and rotate within the bore and to have an end which can extend from and retract towards the manipulation end of the housing, and
a diaphragm situated distal the handle end of the housing and adapted to be inflated and deflated substantially circumferentially from the housing.

Preferably the manipulation means is sealably connected to the bore sufficient to prevent passage of fluid, the seal allowing rotational and reciprocal movement of the manipulation means in relation to the bore.

Preferably the diaphragm is inflated and deflated via a passage associated with the bore which communicates the diaphragm with a source of inflation media.

Preferably the passage includes a means to prevent the uncontrolled deflation of the diaphragm.

Preferably the diaphram is inflated with a sterile saline solution or air.

Preferably the surgical apparatus further comprises a channel adapted to pass a gaseous substance, the channel passing through the manipulation means and having an exit from the portion of the manipulation means which is extendable from the housing.

Preferably the channel extends along or through the housing and has an exit between the manipulation end of the housing and the diaphragm.

Preferably the gaseous substance is carbon dioxide.

Preferably the manipulation means further comprises a releasably attachable tip.

The invention further comprises a method of laparoscopically assisted vaginal hysterectomy utilising a surgical apparatus which includes a diaphragm adapted to be inflated and deflated substantially radially from a housing, and manipulation means in the form of a rod adapted to extend from the housing and to rotate and reciprocate in relation to the housing;
the method comprising the steps of inserting the apparatus with the diaphragm in a deflated condition into the vagina, inflating the diaphragm to fix the apparatus in position and to seal the vagina, utilising the manipulation means to manipulate the uterus from within the uterus prior to the vaginal cut and to manipulate the uterus from outside the uterus after the vaginal cut.

The invention further comprises a method of laparoscopically assisted vaginal hysterectomy utilising a surgical apparatus which includes a diaphragm adapted to be inflated and deflated substantially circumferentially from a housing, manipulation means in the form of a rod adapted to extend from the housing and to rotate and reciprocate in relation to the housing, and a gas channel adapted to extend through the rod;
the method comprising the steps of inserting the apparatus with the diaphragm in a deflated condition into the vagina, inflating the diaphragm to fix the apparatus in position and to seal the vagina, passing a gas through the gas channel and into the peritoneal and abdominal cavity to create a pneumoperitoneum, utilising the manipulation means to manipulate the uterus from within the uterus prior to the vaginal cut and to manipulate the uterus from outside the uterus after the vaginal cut.

Preferably the method includes use of a mechanical means to manipulate the surgical apparatus during the course of the vaginal hysterectomy.

DRAWINGS

A preferred form of the invention will now be described with the aid of the accompanying drawings, wherein.

DETAILED DESCRIPTION OF THE INVENTION

Figure 1:
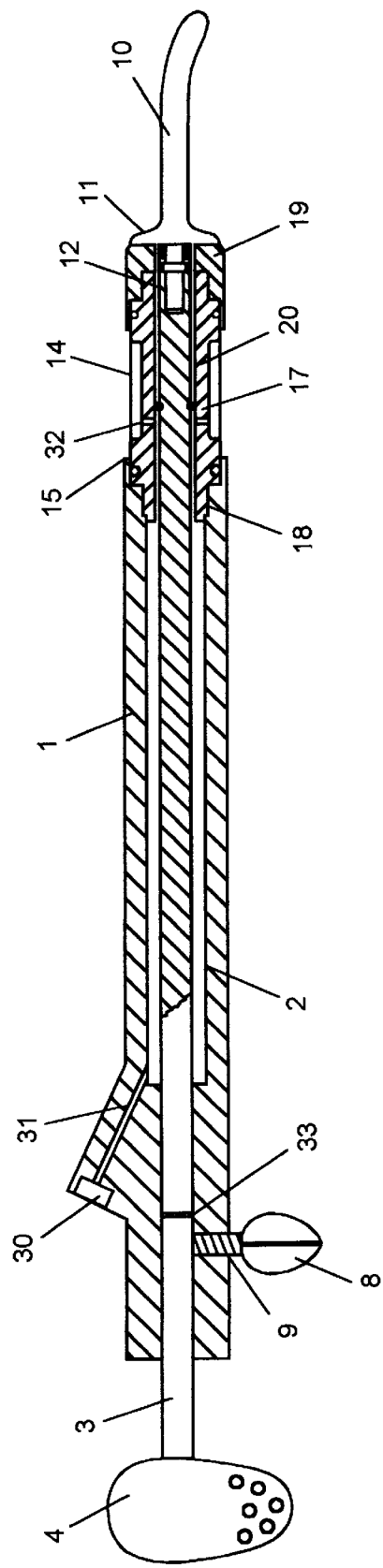
FIG. 1 is a diagrammatic longitudinal sectional view of the apparatus showing the diaphragm in a deflated condition.
Figure 2:
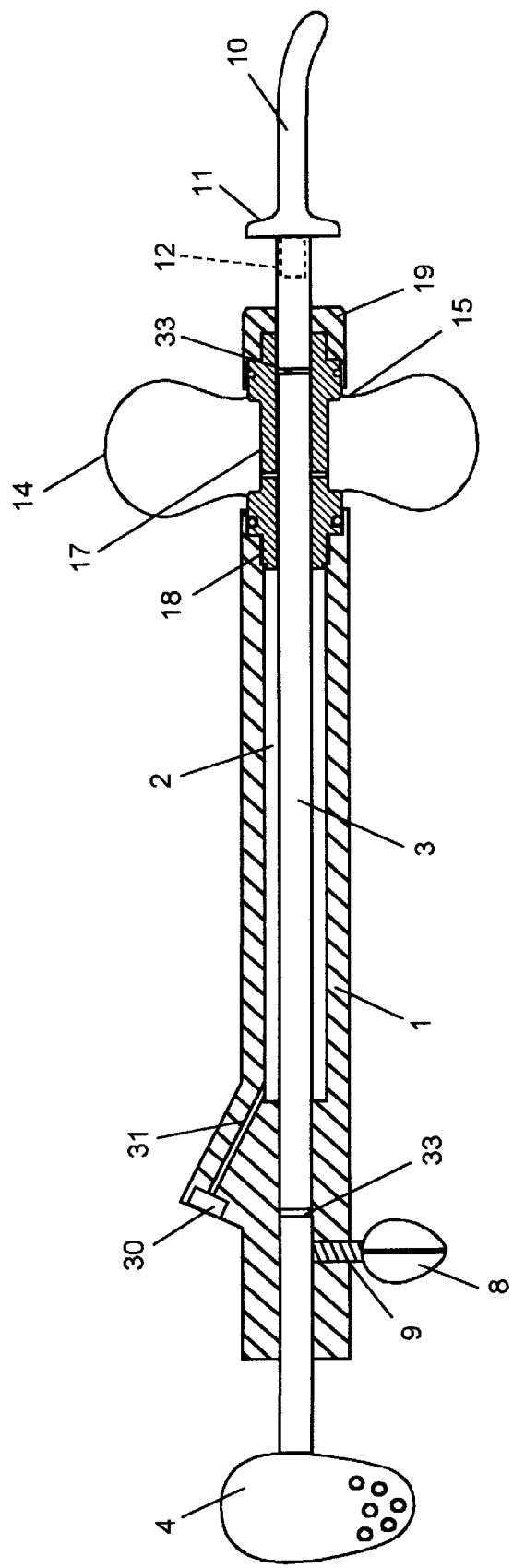
FIG. 2 is a similar view of the apparatus of FIG. 1, but illustrating the diaphragm in an inflated condition.

As illustrated in the drawings, the apparatus, which may be formed entirely or partly from a plastics material or materials, comprises a housing 1 which can be an elongated tube having a bore 2. The apparatus may also be formed of other suitable materials, such as stainless steel, as will be known in the art. A rod 3 which is longer than the housing is engaged within the bore in a manner that it can have both reciprocatory and rotatory movement in the bore. One end of the rod, herein the handle end, is provided with a handle 4 which can conveniently be in the form of an enlargement. The housing is provided with a thumbscrew 8 which may have a suitably threaded shank 9 which can be threaded into a radial hole formed in the housing, with the thumbscrew being so formed that it can be rotated to bear against the rod to lock it in a desired position. The distal end of the rod is formed into a tip 10 which may be curved as illustrated in the drawing. Alternative configurations can be applied to the tip as required. Preferably the rod is also provided with an annular stop 11 which will limit the retraction of the rod 3 into the bore 2 of the housing As can be seen from the drawings, the curved tip can be removably attached to the rod 2 such as by forming a spigot and socket joint 12 so the curved tip can engage the end of the rod 3.

Figure 3:
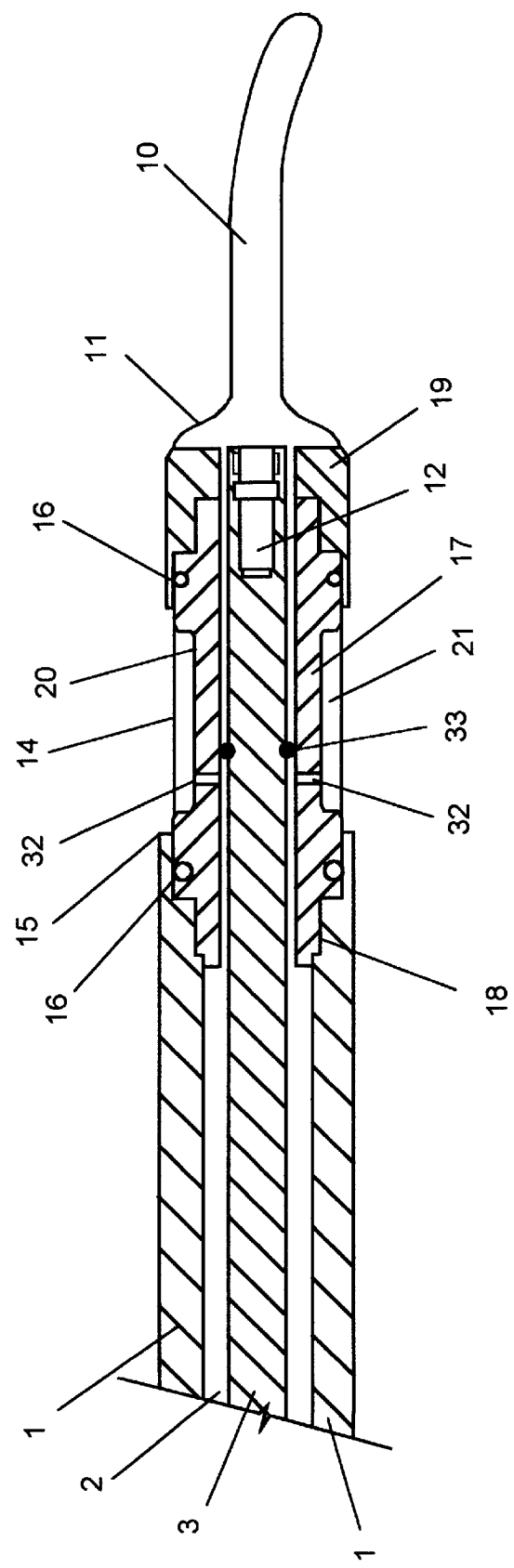
FIG. 3 is an enlarged view of part of FIG. 1.

The apparatus also includes an inflatable diaphragm 14 and means to inflate and deflate the diaphragm. In a highly preferred form, the diaphragm is of a balloon like construction and is sealed at 15 to the housing 1. The diaphragm can be constructed from any suitable material as will be known in the art. Plastics materials such as latex or the like are preferred. Preferably O rings 16 are utilised for the sealing of the diaphragm to the housing, but other satisfactory methods of sealing the diaphragm to the housing can also be utilised. In the construction illustrated, the diaphragm is located on the housing by a diaphragm boss 17 one end of which is fixed at 18 to the housing and the other end fixed to a housing extension 19. In the form of the diaphragm boss 17 illustrated, part of the boss is waisted as at 20 so a gap 21 (see FIG. 3) is formed between the periphery of the boss 20 and the inside of the diaphragm 14.

The means to inflate and deflate the diaphragm 14 may comprise an inlet 30 into which a one way valve (not shown in the drawings) may be engaged, with the inlet 30 communicating with a duct 31 which extends through the housing and forms part of the bore of the housing. An orifice or orifices 32 are formed in the boss 17 in a manner that the duct 31 will communicate with the gap 21 between the waisted portion of the boss 17 and the underside of the diaphragm.

Preferably the rod 3 and the bore 2 are sealed to each other to prevent escape of fluid from the duct 31. In a preferred form, this seal is arranged by O rings 33 which are engaged on the rod and which bear against the wall of the bore 2 so that longitudinal or rotatory movement of the rod will not allow fluid to escape. The diaphragm may be inflated, for instance by passing an inflation media, such as a sterile saline solution, air or the like under pressure through the one way valve which can be manipulated when required to deflate the diaphragm. Although the particular method of inflating the diaphragm by means of the one way valve and the duct 31 are described, it is to be understood this is one form only of a suitable method of inflating and deflating the diaphragm and other arrangements which will provide the desired effect can also be employed.

Figure 4:
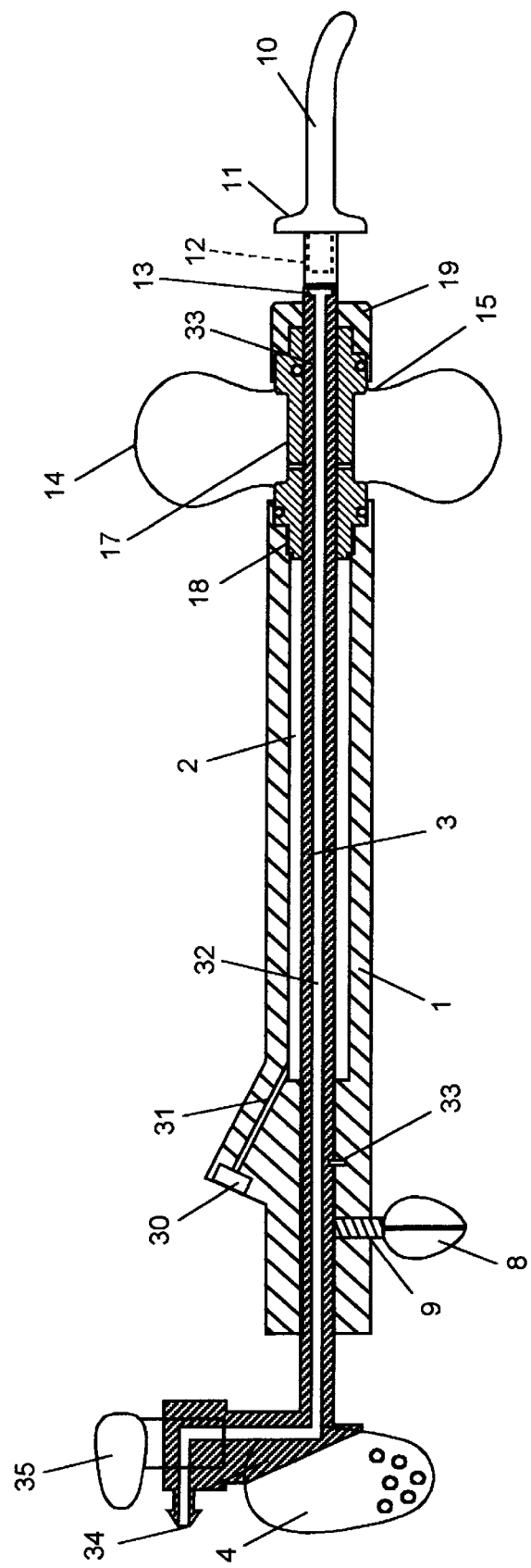
FIG. 4 is a diagrammatic longitudinal sectional view of a preferred form of the apparatus having a gas channel and showing the diaphragm in an inflated condition.

With reference to FIG. 4, a preferred form of the surgical apparatus comprises a housing 1 having a bore 2 containing a rod 3. The rod 3 contains a gas channel 36 which extends substantially through the center of the rod 3. The apparatus further comprises a nipple 34 for gas entry, and a valve means 35 which controls the flow of gas into the gas channel 36. As shown in FIG. 4, both the nipple 34 and the valve means 35 are present at the end of the rod 3 which Is distal the diaphragm 14 end of the apparatus. The gas channel 36 exits the rod 3 via an opening 37 which is situated adjacent the spigot and socket joint 12 at the end of the rod 3. The opening 37 should be situated on the rod 3 such that, in use, the opening 37 allows gas into the peritoneum, while the vaginal opening has been sealed by the inflated diaphragm 14.

The preferred form of the apparatus as shown in FIG. 4 has the gas channel 36 in the rod 3. Alternative positioning of the channel, as will be known in the art, may be used as well. For example, the channel could pass through or along the housing with an exit between the diaphragm 14 and the end of the housing from which the rod 3 extends. The essential feature is that the gas exits the apparatus beyond the diaphragm 14 when the diaphragm 14 is inflated. This will seal the peritoneal cavity and the pneumoperitoneum can be created by entry of a suitable gas through the apparatus and into the peritoneal cavity toward the top of the vagina. The gas emerges just prior to the cervix, distending the upper vagina with gas which in turn allows gas to pass into the peritoneal and abdominal cavity thus insulating the abdomen and pelvis from below after the vaginal seal has been created by inflation of the diaphragm 14. This allows easier insertion of the trochars when the laparoscopic portion of the surgery is commenced and distances the bowel from the trochar tips at insertion. It also allows the operator to have complete confidence in where the gas is being inserted rather than the blind insertion through a Verres needle which is the most commonly used method.

The means by which gas enters the gas channel, shown as nipple 34 in FIG. 4, can be any suitable means as will be known in the art. In addition, the gas used to create the pneumoperitoneum can be any suitable gas as will be known in the art. Carbon dioxide or similar gaseous substances can be used as are standard in such techniques.

The surgical apparatus of the present invention is intended to enhance the laparoscopically assisted vaginal hysterectomy (LAVH) procedure by creating and/or maintaining the pneumoperitoneum for the maximum possible time.

The LAVH process is well known and has been described, inter alia in Reich et al, J. Gynaecol. Surg. 1989, 5, p. 213–216. In laparoscopic procedures, the surgery is performed in the interior of the abdomen through a small incision. In order to allow access to the internal organs, a pneumoperitoneum is created as a result of which the abdomen is inflated in order to enable the surgeon to perform the operation. However, with laparoscopically assisted vaginal hysterectomies (LAVH) is it is desirable to seal the vagina in order to prevent escape of the gas during the procedure.

To utilise the apparatus as herein described, surgery begins in the standard manner for routine vaginal hysterectomies. Using a scalpel, the cervix is circumscribed, the bladder dissected free of the lower uterine segment and the utero-vesical fold of the peritoneum open thus entering the pelvic cavity. The Pouch of Douglas is entered through the posterior fornix. The utero-sacral ligaments are then clamped and divided and ligated. This completes the initial vaginal part of the dissection.

The surgical apparatus of the present application in now passed into the vagina with the diaphragm 12 deflated. The curved tip 8 is passed through the cervix of with the direction of the curve aimed at the uterine fundus. If the uterus is in a retroverted position, turning the handle 4 will help convert the position to anteversion. The diaphragm 12 is then inflated with between 100 and 150 mls of normal saline solution via the one way valve. This fixes the vaginal seal in position within the vagina and also seals the upper vagina in an airtight fashion. The handle 4 is pushed forward which in turn pushes forward the curved tip 8 which will further distance the ureters from the lateral border of the cervix. The thumb screw 5 is used to fix the position of the rod 3 within the housing 1.

Generally, in order to produce the pneumoperitoneum via means other than as shown in FIG. 4, the laparoscope is passed into the abdomen after direct trocar entry through a vertical midline incision at the inferior umbilical verge. When entry into the peritoneal cavity has been confirmed by direct vision, carbon dioxide gas is pumped in through a standard insulator. Alternative methods of creating a pneumoperitoneum as will be known to a person skilled in the art may also be used.

If the surgical apparatus comprises a gas channel 36, as is shown in the apparatus of FIG. 4, the pneumoperitoneum will be formed by opening the valve means 35 to allow a suitable gas, such as $CO_2$, to pass through the gas channel 36 and exit the apparatus via the opening 37. The gas will pass from the upper vagina into the abdomen and pelvis forming the pneumoperitoneum. Once the pneumoperitoneum is satisfactory the valve means 35 can be closed or a continuous top up insufflation can be achieved by maintaining the valve means 35 in a suitably open position. The gas can be supplied to the apparatus via the nipple 34 and can be supplied by standard, known insulators.

Following the creation of the pneumoperitoneum it is with relative ease that staples can be applied down the length of the broad ligament. The uterine artery can be transected, the upper vagina entered, thus freeing the uterus from all attachments to the body. The uterus will now be completely devascularised and, no matter how large, it can be cut into as many pieces as is required to enable it to be extracted through the vagina without difficulty and additional blood loss.

As will be known in the art, robotic manipulators have been used relatively recently to assist surgical procedures. Robotic manipulators can be surgeon-controlled with the advantage that there is a substantial lessening of human fatigue in the performance of the surgery. One difficulty in such robotic assisted surgery when applied to uterine surgical procedures, is that It is preferable for a fulcrum point to be provided within the vagina, around which the robotic manipulator can exercise degrees of movement. As will be apparent to a person skilled in the art, the diaphragm, when inflated, can be used to provide a suitable fulcrum point for such robotic assisted manipulation.

Figure 5:
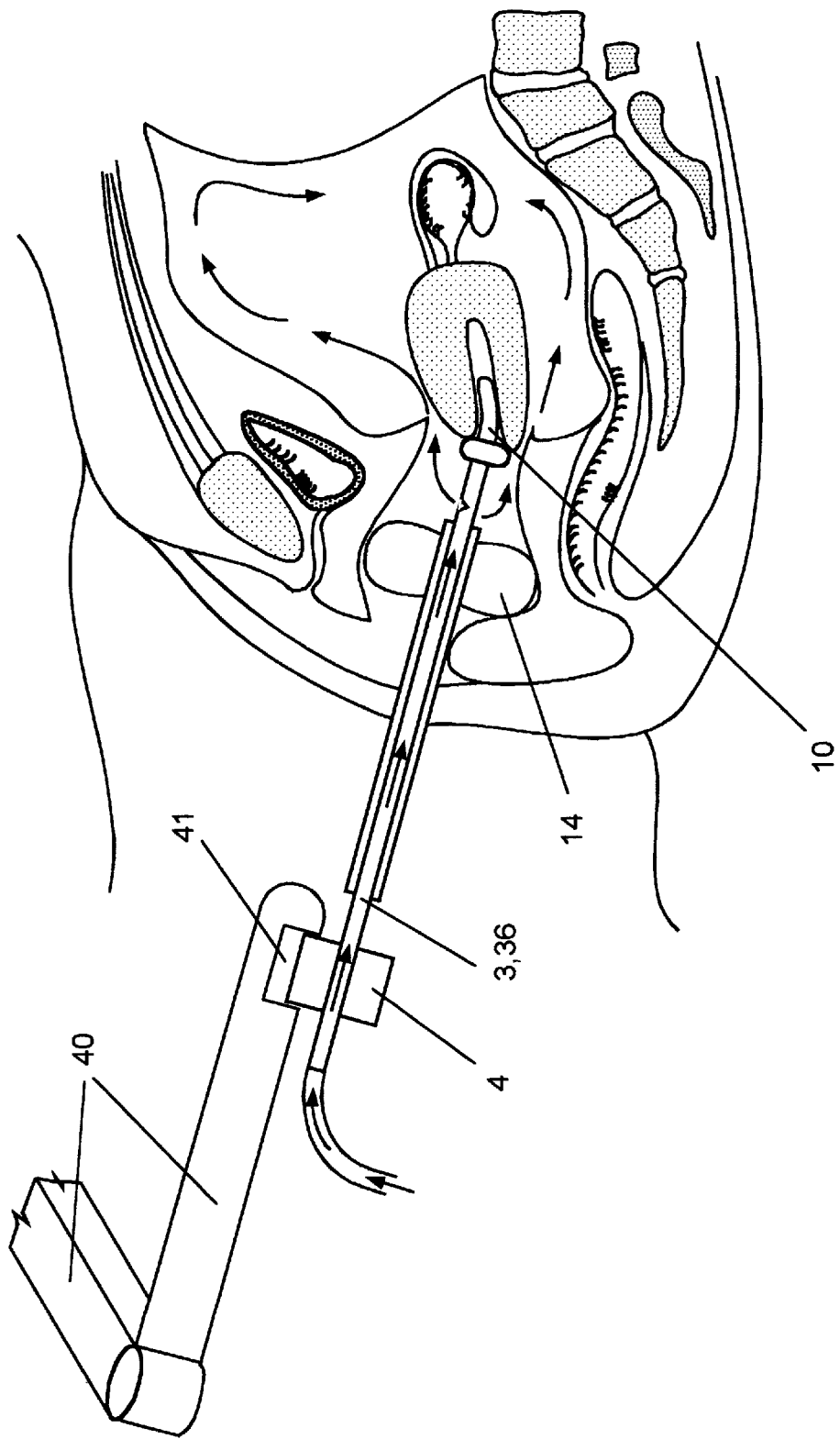
FIG. 5 is a schematic representation of a preferred form of the apparatus when used in conjunction with a mechanical manipulation means.

With reference to FIGS. 4 and 5, the inflated diaphragm 14, can be used to provide a fixed, cushioned, fulcrum point within the vagina to allow the rod 3 and the tip 10 to move about the fulcrum point so formed. Movement in the upward, downward and right/left arcs will be readily achievable. The rod 3 can also move in a reciprocal manner within the bore 2 and a gas can still pass into the peritoneal cavity via the gas channel 36 (if the channel 36 is present in the apparatus) as has been described previously. In FIG. 5, the rod 3 and gas channel 36 are shown as one combined feature for ease of reference. The control of the entry of gas to the apparatus can be external of the apparatus as indicated, but not shown, in FIG. 5. The robotic manipulation can be achieved by any suitable means as will be known in the art. A robotic arm 40, as shown in FIG. 5, can be attached by any suitable means, such as the socket 41 in FIG. 5, to the handle 4 of the apparatus to provide the connection between the apparatus of the present invention and the robotic manipulation means.

The surgical apparatus of the present invention therefore has the capacity to enhance the ability of a surgeon-controlled mechanical arm to manipulate the uterus into all the positions that a human assistant would otherwise do with the advantage of less human fatigue and less damage to the upper vagina.

The foregoing describes various preferred forms ofthe apparatus. Alterations and modifications can be made to the apparatus within the general concept as disclosed as will be obvious to a person skilled in the art. All such alterations and modifications are intended to be included within the scope of the invention as defined by the appended claims.

What is claimed is:

1. A surgical apparatus comprising:
   (a) an elongated housing, having a handle end and a manipulation end;
   (b) a bore extending through the housing;
   (c) a manipulation means comprising a rod which extends through the bore in the housing with an end portion which extends from the manipulation end of the elongated housing, which rod is reciprocally movable and rotatable within the bore of the housing to enable the end portion of the rod to be further extended from or retracted towards and rotated about the manipulation end of the housing, and a tip part extending beyond the end portion of the rod;
   (d) a diaphragm situated distal the handle end of the housing and adapted to be inflated and deflated substantially circumferentially from the housing; and
   (e) a channel for passing a gas from the end portion of the rod past the diaphragm, extending along or through the rod and having an exit in or adjacent to the end portion of the rod between the manipulation end of the housing and the tip part extending beyond the end portion of the rod.

2. An apparatus according to claim 1 comprising a passage extending from the handle end of the elongated housing to the diaphragm for inflating the diaphragm.

3. An apparatus according to claim 2 wherein said passage includes means to prevent uncontrolled deflation of the diaphragm.

4. A surgical apparatus according to claim 1, wherein the manipulation means further comprises a releaseably attachable tip.

5. A surgical apparatus comprising:
   (a) an elongated housing having a handle end and a manipulation end;
   (b) a bore extending through the housing;
   (c) manipulation means comprising a rod adapted to reciprocate and rotate within the bore and having a handle on one end of the housing and a portion which extends from and retracts toward the manipulation end of the housing at the other end of the housing, and a tip part extending beyond the end portion of the rod;

(d) a diaphragm situated distal the handle end of the housing and adapted to be inflated and deflated substantially circumferentially from the housing via a passage associated with the bore; and (e) a gas channel passing through the rod and having an exit from the portion of the rod between the manipulation end of the housing and the tip part extending beyond the end portion of the rod.

6. A surgical apparatus according to claim 5, wherein the manipulation means further comprises a releaseably attachable tip.

7. A method of laparoscopically assisted vaginal hysterectomy, the method utilizing a surgical apparatus which includes a diaphragm adapted to be inflated and deflated substantially circumferentially from a housing; a rod which extends through the housing and from a manipulation end of the housing and which can rotate and reciprocate in relation to the housing, and a gas channel which extends through the rod, the method comprising the steps of:

(a) inserting the apparatus with a diaphragm in a deflated condition into a vagina;

(b) inflating the diaphragm to fix the apparatus in position and to seal the vagina;

(c) passing a gas through the gas channel and into a peritoneal and abdominal cavity to create a pneumoperitoneum;

(d) utilizing the rod to manipulate the uterus from within a uterus prior to the vaginal cut; and (e) utilizing the rod to manipulate the uterus from outside the uterus after the vaginal cut.

8. A method according to claim 7 including manipulating the surgical apparatus by means of a robotic arm attached to the apparatus.

* * * * *